(12) United States Patent
Tseng et al.

(10) Patent No.: US 7,700,279 B2
(45) Date of Patent: Apr. 20, 2010

(54) ASSAY FOR BCR/ABL GENE REARRANGEMENT

(75) Inventors: Richard W. Tseng, Mission Viejo, CA (US); Michael K. Samoszuk, Rancho Santa Margarita, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 431 days.

(21) Appl. No.: 10/742,616

(22) Filed: Dec. 18, 2003

(65) Prior Publication Data

US 2005/0037373 A1 Feb. 17, 2005

Related U.S. Application Data

(63) Continuation-in-part of application No. 09/747,165, filed on Dec. 22, 2000, now abandoned.

(60) Provisional application No. 60/173,050, filed on Dec. 24, 1999.

(51) Int. Cl.
C12Q 1/68 (2006.01)
C12P 19/34 (2006.01)
C07H 21/04 (2006.01)

(52) U.S. Cl. .................. 435/6; 435/91.2; 536/24.31; 536/24.32; 536/24.33

(58) Field of Classification Search .................. 435/6; 536/24.31, 24.32, 24.33
See application file for complete search history.

(56) References Cited

OTHER PUBLICATIONS

ABI prism User bulletin #5 (1998).*
Kreuzer, KA et al. Lightcycler technology for the quantitation of bcr/abl fusion transcripts. Cancer Res., vol. 59, pp. 3171-3174, Jul. 1, 1999.*
Hariharan et al. cDNA sequence for human BCR, the gene that translocates to the abl oncogene in chronic meloid leukemia. EMBO J. vol. 6(1): pp. 115-119, 1987.*
Eder, M et al. Monitoring of BCR-ABL expression using real-time RT-PCR in CML after bone marrow or peripheral blood stem cell transplantation. Leukemia, vol. 13, pp. 1383-1389, 1999.*
Emig, M et al. Accurate and rapid analysis of residual disease in patients with CML using specific fluorscent hybridization probes for real time quantitative RT-PCR. Leukemia, vol. 13, pp. 1825-1832, 1999.*
Mensink, E et al. Quantitation of minimal residual disease in Philadelphia chromosome positive chronic myeloid leukaemia patients using real-time quantitative RT-PCR. British J Haematology, vol. 102, pp. 768-774, 1998.*
Lowe et al. A computer program for selection of oligonucleotide primers for polymerase chain reactions. Nucleic Acids Research, vol. 18, No. 7, pp. 1757-1761, 1990.*
Aldea et al., "Rapid detection of herpes simplex virus DNA in genital ulcers by real-time PCR using SYSBR green 1 dye as the detection signal." J. Clin. Microbiol. 40(3):1060-1062 (2002).

Buck, et al., "Design strategies and performance of custom DNA sequencing primers." Biotechniques, 27:528-536 (1999).
Catovsk D., "Ph1 positive acute leukemia and chronic granulocytic leukemia: one or two disease." Br. J. Haematol 42: 493-498 (1979).
Clark S. S. et al., "Unique forms of the abl tryrosine kinase distinguish PH-positive CML from PH-positive ALL." Science 235:85-88, (1987).
Dehee et al., "Quantitation of HTLV-1 proviral load by a Taqman Real time PCR assay." J. Virol. Meth. 102:37-51 (2002).
Eder et al, "Monitoring of BCR-ABL expression using Real-time RT-PCR in CML after bone marrow or peripheral blood stem cell transplantation." Leukemia 13:1383-1389 (1999).
Ercolani et al., "Isolation and complete sequence of a functional human Glyceraldehyde 3 phosphate dehydrogenase gene." J. Biol. Chem. 263(30):15335-15341 (1988).
Gibson et al., "A novel method for real-time quantitative RT-PCR." Genomic Res. 6: 995-1001 (1996).
Hariharan et al., "cDNA sequence for human BCR, the gene that translocates to the abl oncogene in chronic myeloid leukemia." EMBO J. 6(1):115-119 (1987).
Kämpke et al., "Efficient primer design algorithms." Bioinformatics, 17:214-225, (2000).
Kawasaki et al., "Diagnosis of chronic myelogenous and acute lymphocytic by detection of leukemia-specific mRNA sequences in vitro." Proc. Natl. Acad. Sci USA 85: 5698-5702 (1988).
Konopka J.B. et al., An alternative of the human c-abl protein in K562 leukemia cells unmasks associated Tyrosine kinase activity. Cell 37:1035-1042 (1984).
Kreuzer et al., "Applicability of an Absolute Quantitative Procedure to Monitor Intra-individual bcr/abl Transcript Kinetics In Clinical Samples from Chronic Myelogenous Leukemia Patients" Int. J. Cancer: 86:741-746 (2000).
Messink et al., "Quantitation of minimal residual diseases in Philadelphia chromosome positive chronic myeloid leukemia patients using real time quantitative PCR." British J. Haemotology 102:768-774 (1998).
Prist et al. "Philadelphia chromosome positive childhood acute lymphocytic leukemia." Blood 56: 15-22 (1980).
Robertson and Walsh-Weller, "An Introduction to PCR Primer Design and Optimization of Amplification Reactions." Methods of Mol. Biol., 98:121-126.
Roche Molecular Biochemicals, Technical Note No. LC Oct. 2000, "Overview of LightCycler Quantification Methods."
Rowley, J.D. et al. "A new consistent chromosomal abnormality in chronic myelogenous leukemia identified by quinacrine fluorescence and giemsa staining." Nature 243: 290-293 (1973).
Shtivelman et al., "Alternative splicing of RNAs transcribed from the human abl gene and from the bcr-abl fused gene." Cell, 47:277-284 (1986).
Wang et al., "Primers are Decisive for Sensitivity of PCR." Biotechniques, 12:82-85 (1994).

\* cited by examiner

*Primary Examiner*—Suryaprabha Chunduru
(74) *Attorney, Agent, or Firm*—Foley & Lardner LLP

(57) ABSTRACT

The present invention provides a simple high-throughput assay for detecting bcr/abl translocations. The method includes qualitative PCR methods for identifying the particular amplified translocation (e1a2 or b2a3/b3a2) and real time PCR for quantifying an amount of bcr/abl transcript (e1a2, b2a3 and b3a2). Quantitative measurement of bcr/abl transcript in accordance with the methods of the invention is useful for monitoring response to therapy.

28 Claims, No Drawings

ASSAY FOR BCR/ABL GENE REARRANGEMENT

This application is a continuation-in-part of U.S. application Ser. No. 09/747,165, filed Dec. 22, 2002, which claims priority under 35 U.S.C. §119(e) from U.S. Provisional Patent Application Ser. No. 60/173,050 filed Dec. 24, 1999. The contents of U.S. application Ser. No. 09/747,165, and provisional application Ser. No. 60/173,050 are incorporated herein by reference thereto.

FIELD OF THE INVENTION

The present invention relates to assay methods which allow for the specific detection, and quantitation of bcr/abl gene rearrangements

BACKGROUND OF THE INVENTION

The following description of the background of the invention is provided simply as an aid in understanding the invention and is not admitted to describe or constitute prior art to the invention.

The Philadelphia chromosome (Ph) is a translocation between chromosome 9 and 22 t(9;22) (q34;q11) that is found in more than 90-95% of chronic myeloid leukemia (CML), about 20-25% of adult, and 2-10% of childhood acute lymphoblastic leukemia (ALL). See Rowley J O (1973), *Nature* 243: 290-293. Catovsk (1979) *Br. J. Haematol.* 42: 493-498; Prist, et al. (1980) *Blood* 56: 15-22. In CML, most of the translocation falls in the major breakpoint cluster region (M-bcr) of the bcr gene, and results in two bcr/abl mRNA molecules with a b2a2 or b3a2 junction which encode $p210^{bcr/abl}$ fusion protein. See Konopka, et al., (1984) *Cell* 37: 1035-1042. In ALL, about two thirds of the bcr breakpoint falls in the minor breakpoint cluster region (m-bcr), and the hybrid bcr/abl transcript contains an e1a2 junction and is translated as a $p190^{bcr/abl}$ fusion protein. See Clark, et al. (1987) *Science* 235: 85-88. Because CML is a clonal disease, detection of bcr/abl fusion transcripts should precisely reflect CML disease activity. bcr/abl mRNA can be specifically and efficiently detected by the reverse transcription—polymerase chain reaction (RT-PCR), because this fusion gene is leukemia specific and can be used as a marker to identify residual disease after therapy. Quantitative RT-PCR detection of bcr/abl fusion is well established in CML diagnostics, and PCR positivity is virtually diagnostic of this type of leukemia. Kawasaki, et al., (1988) *Proc Natl Acad Sci (USA)* 85: 5698-5702. Gibson, et al., (1996) *Genomic Res* 6:995-1001.

However, the present methods of CML or ALL diagnostics are lacking in that for the qualitative assay (that is indication of presence or absence of the disease and not a quantitative number of cells present or other quantitative information provided) uses hazardous radioactive isotopes, complex hybridizations and takes about five days. Further, the present methods do not provide for a single container method of assaying for all three translocation products and providing reproducible and easily and meaningfully interpretable results.

Accordingly, it would be desirable to provide assay methods for bcr/abl translocations that are convenient to carry out, provide highly reproducible qualitative and quantitative results and in which all three translocations may be assayed for at once in one container.

SUMMARY OF THE INVENTION

The present invention provides methods and compositions for determining the presence of bcr/abl translocations characteristic of CML and AML.

In various embodiments of the present invention, oligonucleotide primers and probes are used in the methods described herein to provide the bcr/abl translocation assay. Thus, in certain embodiments, the invention relates to primer sequences that can optionally be used together to amplify nucleic acid sequences for simultaneous detection of bcr/abl translocations which may be present in a sample. Primer based amplification and detection of amplified sequence by hybridization with molecular beacon labeled probes are conducted together using a real time PCR format. Differentially detectable molecular beacon pairs of labels can be used when multiple probes are combined in the same assay.

In additional embodiments, the invention relates in part to probe nucleic acids that can be conjugated to a detectable label, preferably, a fluorescent dye, and most preferably a dye pair located at or near the 5' and 3' end of the oligonucleotides. In some embodiments, the probes are labeled with molecular beacon pairs of labels.

In a first aspect, the invention relates to a composition of one or more oligonucleotides having primer sequences for amplifying bcr/abl translocation selected from a sequence consisting essentially of any one of SEQ ID NOs 1-3.

In another aspect, the invention relates to a composition of one or more oligonucleotides which can be used as a labeled probe for detecting amplified bcr/abl translocation selected from a sequence consisting essentially of any one of SEQ ID NOs 8 and 9.

In a related manner, the invention includes a composition of one or more oligonucleotides having primer sequences for amplifying a housekeeping gene, abl or GAPDH, using as primers a sequence consisting essentially of SEQ ID NOs 4 and 5 (abl) or 6 and 7 (GAPDH). Also provided is oligonucleotide SEQ ID NO: 10 which can be labeled for detection of amplified abl and oligonucleotide SEQ ID NO:11 which can be labeled for detection of amplified GAPDH.

In preferred embodiments, one or more of the selected oligonucleotides can be conjugated to a detectable label, preferably a fluorescent dye, and most preferably a beacon dye pair. Particularly preferred oligonucleotide dye conjugates are 5'[2'-chloro-7'-phenyl-1,4-dichloro-6-carboxyfluorescein (VIC)]-CTG CCC ACA GTA CC-3' (SEQ ID NO: 12); 5'[6-carboxyfluorescein(FAM)]-TGC CCA CGG TAC C-3' (SEQ ID NO: 13); and 5-tetrachloro-6-carboxyfluorescein (TET)]-ACC CAG GCC CAC AT-3' (SEQ ID NO: 14). In further embodiments, these dye labeled probes also are labeled with a quencher moiety. Labeled oligonucleotide may be used as probes in methods to detect bcr/abl translocations present in a test sample.

In another aspect, the present invention relates in part to methods for detecting the presence of a bcr/abl translocation is present in a biological sample. The method comprises:

a) contacting RNA or cDNA from the biological sample with oligonucleotide primers SEQ ID NO. 1-3 and with bcr/abl e1/a2 transcript probe SEQ ID NO: 8 and bcr/abl b2a2/b3a2 transcript probe SEQ ID NO: 9 wherein said probes are labeled with a molecular beacon pair;

b) conducting amplification by temperature cycling with a DNA polymerase with 5' exonuclease activity, wherein binding of the probe to amplified nucleic acid results in degradation of the probe during DNA synthesis; and c) monitoring the accumulation of amplified nucleic acid in real time by detecting an increase in reporter dye fluorescence over time, wherein an increase in reporter dye fluorescence indicates the presence of a bcr/abl translocation in the biological sample.

In one embodiment, the method further comprises determining a housekeeping gene transcript signal present in the biological sample. The additional method steps comprise:

d) contacting the RNA or cDNA of the biological sample with a primer pair for amplifying a housekeeping gene transcript and a probe for the amplified housekeeping gene labeled with a molecular beacon pair;

e) conducting amplification by temperature cycling with a DNA polymerase with 5' exonuclease activity, wherein binding of the probe to amplified nucleic acid results in degradation of the probe during DNA synthesis; and f) monitoring the accumulation of amplified nucleic acid in real time by detecting an increase in reporter dye fluorescence over time, wherein an increase in reporter dye fluorescence indicates the presence of the housekeeping gene transcript in the biological sample.

In a preferred embodiment, the transcript may be abl or GAPDH.

In another embodiment, the method further comprises the step of correlating the housekeeping gene transcript signal with the amount of a cell RNA or cDNA that generates the same signal. This is achieved by extrapolating the housekeeping gene signal from the biological sample to a standard curve of PCR signals versus cell line RNA or cDNA obtained by amplifying using steps d) and e) but with the cell line RNA or cDNA, respectively. The amount of cell line RNA or cDNA that has the same housekeeping gene transcript signal as in the biological sample provides a more uniform value to which bcr/abl transcript PCR signals can be compared. The ratio of bcr/abl transcript to cell line RNA or cDNA correlated to housekeeping gene transcript signal in the biological sample provides a "quantitative" estimate of leukemic cells with a bcr/abl translocation genetic signature in the sample.

In another aspect, the present invention relates to methods for determining if a blood or bone marrow sample contains CML or AML cells characterized in having a particular bcr/abl translocation. The method comprises:

a) contacting RNA or cDNA from a biological sample with:
  i) oligonucleotide primers SEQ ID NO. 1 and 3 and bcr/abl e1/a2 transcript probe SEQ ID NO: 8, or
  ii) oligonucleotide primers SEQ ID NO: 2 and 3 and bcr/abl b2a2/b3a2 transcript probe SEQ ID NO: 9, wherein the probes are labeled with a molecular beacon pair;

c) conducting amplification by temperature cycling with a DNA polymerase with 5' exonuclease activity, wherein binding of the probe to amplified nucleic acid results in degradation of the probe during DNA synthesis; and d) monitoring the accumulation of amplified nucleic acid in real time by detecting an increase in reporter dye fluorescence over time, wherein an increase in reporter dye fluorescence indicates the presence of the particular bcr/abl translocation in the biological sample.

In accordance with the method, either the bcr/abl e1/a2 probe signal will result or the b2a2/b3a2 probe signal will result. If the latter case is present, the amplified product is evaluated by gel electrophoresis to distinguish the size of the amplified product wherein a size of about 124 bp indicates b2a2 and a size of about 199 bp indicates b3a2.

In the above methods, the primer pairs and probes for detecting bcr/abl and the primer pair and probe for detecting a housekeeping gene transcript can be combined in a single tube and amplified together. In such embodiment, the various probes used are labeled with distinguishing molecular beacon pairs.

In another aspect the present invention provides kits for one of the methods described herein. In various embodiments, the kits contain one or more of the following components in an amount sufficient to perform a method on at least one sample: one or more primers of the present invention, devices for performing the assay, which may include one or more probes that hybridize to amplified bcr/abl transcript or housekeeping gene transcript, and optionally contain buffers, enzymes, and reagents for performing amplification.

DETAILED DESCRIPTION OF THE INVENTION

The present invention provides specific primers and probes that aid in the detection of cells with RNA transcripts encoding bcr/abl translocation and the detection of transcripts of particular housekeeping genes which are useful as a reference for quantitatitive estimation of leukemic cell load.

The term "bcr/abl translocation" or "t(9;22)" as used herein is an aberrant gene rearrangement between the abl protooncogene on chromosome 9 and the breakpoint cluster region (bcr) on chromosome 22. The breakpoint is constant at the abl locus occurring 5' to exon 2 in an approximately 200 kb region of the abl gene. In contrast, the breakpoint for bcr but occurs at two primary and distinct areas within bcr. These are termed the major (M) and minor (m) breakpoint cluster regions. The major breakpoint transcripts are at b2a2 and b3a2 and encode p210 fusion protein, which are typically seen in CML. The minor breakpoint transcript is at e1a2 and encodes p190 fusion protein, which is typically seen in ALL.

The detection of t(9;22) is supportive of a clinical diagnosis of chronic myelogenous leukemia (CML). Detection of t(9;22) is also useful in the distinction of reactive causes of persistent leukocytosis from CML, the distinction of CML from other chronic myeloproliferative disorders (e.g. polycythemia vera, essential thrombocythemia, and agnogenic myeloid metaplasia), and the distinction of CML from chronic myelomono-cytic leukemia. A subset of acute lymphoblastic leukemia (ALL) contain the t(9;22). The identification of the t(9;22) has adverse prognostic implications in ALL.

The term "housekeeping gene" as used herein refers to genes that are generally always expressed and thought to be involved in routine cellular metabolism. Housekeeping genes are well known and include such genes as glyceraldehyde-3-phosphate dehydrogenase (G3PDH or GAPDH), albumin, actins, tubulins, cyclophilin, hypoxanthine phsophoribosyltransferase (HRPT), L32. 28S, and 18S rRNAs and abl.

The term "oligonucleotide" as used herein refers to a short polymer composed of deoxyribonucleotides, ribonucleotides or any combination thereof. These oligonucleotides are at least 9 nucleotides in length, preferably 20 to 70 nucleotides long, with 21 to 26 nucleotides being the most common. In certain embodiments, the oligonucleotides are chemically linked or otherwise associated with a detectable label.

The term "isolated" as used herein with reference to a nucleic acid (e.g., an RNA, DNA or a mixed polymer) refers to one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

The term "substantially pure" as used herein is a nucleic acid that represents more than 50% of the nucleic acid in a sample. The nucleic acid sample may exist in solution or as a dry preparation. Oligonucleotides, primers and probes of the invention are preferably substantially purified.

The term "primer" as used herein means a sequence of nucleic acid, preferably DNA, that hybridizes to a substantially complementary target sequence and is recognized by DNA polymerase to begin DNA replication.

The term "hybridize" as used herein refers to process that two complementary nucleic acid strands anneal to each other under appropriately stringent conditions. Hybridizations are typically and preferably conducted with probe-length nucleic acid molecules, preferably 20-100 nucleotides in length. Nucleic acid hybridization techniques are well known in the art. See, e.g., Sambrook, et al., 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology. John Wiley & Sons, Secaucus, N.J.

The term "stringent hybridization conditions" as used herein refers to hybridization conditions at least as stringent as the following: hybridization in 50% formamide, 5× SSC, 50 mM NaH2PO4, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In another example, stringent hybridization conditions should not allow for hybridization of two nucleic acids which differ over a stretch of 20 contiguous nucleotides by more than two bases.

The term "substantially complementary" as used herein means that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

The term "flanking" as used herein means that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase.

The term "complement" as used herein means the complementary sequence to a nucleic acid according to standard Watson/Crick pairing rules. A complement sequence can also be a sequence of RNA complementary to the DNA sequence or its complement sequence, and can also be a cDNA.

The term "coding sequence" as used herein means a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

The term "non-coding sequence" as used herein means a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

The term "amplification" or "amplify" as used herein means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4):852-6, 858, 860 passim.

Primers for amplifying bcr-abl transcripts and transcripts for abl and GAPDH are given in Table 1.

TABLE 1

PCR Primers for amplifying bcr/abl and housekeeping genes

| Primer | Sequence | | Target |
|---|---|---|---|
| BCR-P1F | 5' - CCTCGCAGAACTCGCAACA -3' | (SEQ ID NO. 1) | bcr/abl (e1a2) |
| BCR-P2,P3 F | 5' - GAGCTGCAGATGCTGACCAA -3' | (SEQ ID NO. 2) | bcr/abl (b2a2/b3a2) |
| BCR/ABL-R | 5' - TCAGACCCTGAGGCTCAAAGTC -3' | (SEQ ID NO. 3) | ABL |
| ABL-F: | 5' - TCC TCC AGC TGT TAT CTG GAA GA -3' | (SEQ ID NO. 4) | ABL (housekeeping gene) |

TABLE 1-continued

PCR Primers for amplifying bcr/abl and housekeeping genes

| Primer | Sequence | Target |
|---|---|---|
| ABL-R | 5' - TGG GTC CAG CGA GAA GGT T -3' (SEQ ID NO. 5) | ABL (housekeeping gene) |
| GAPDH-F: | 5' - GAA GGT GAA GGT CGG AGT C -3' (SEQ ID NO. 6) | GAPDH (housekeeping gene) |
| GAPDH-R | 5' - GAA GAT GGT GAT GGG ATT TC -3' (SEQ ID NO. 7) | GAPDH (housekeeping gene) |

The term "probe" as used herein means a sequence of nucleic acid, preferably DNA, that hybridizes to a substantially complementary target sequence. The probe is attached to a solid phase or to a detectable moiety.

The term "detectable label" as used herein refers to a composition or moiety that is detectable by spectroscopic, photochemical, biochemical, immunochemical, electromagnetic, radiochemical, or chemical means such as fluorescence, chemifluoresence, or chemiluminescence, or any other appropriate means. Preferred detectable labels are fluorescent dye molecules, or fluorochromes, such fluorescein, phycoerythrin, CY3, CY5, allophycocyanine, Texas Red, peridenin chlorophyll, cyanine, FAM, JOE, TAMRA, TET, VIC. These examples are not meant to be limiting. Methods and compositions for detectably labeling molecules, such as oligonucleotides, PNA-DNA hybrids, etc. are well known in the art. See, e.g., U.S. Pat. Nos. 6,316,230; 6,297,016; 6,316,610; 6,060,240; 6,150,107; and 6,028,290, each of which are hereby incorporated by reference in their entirety.

The term "fluorochrome" as used herein refers to a molecule that absorbs a quantum of electromagnetic radiation at one wavelength, and emits one or more photons at a different, typically longer, wavelength in response.

The term "molecular beacon pair" as used herein refers to a pair of fluorochromes that exhibit fluorescence energy transfer wherein the fluorochromes are associated in a fixed relationship that resists separation of the pair. Preferably, the fluorochrome pair is physically linked to different locations of a molecule. An energy transfer pair may be excited by a quantum of electromagnetic radiation at a wavelength at which the donor fluorochrome is excited; however, fluorescence from the donor fluorochrome that would be expected in the absence of the acceptor is quenched at least in part, and emission at an emission wavelength of the acceptor fluorochrome is observed. In preferred embodiments, a fluorochrome is one member of a physically linked "molecular beacon" pair.

In these embodiments, the molecular beacon pair may be excited by a quantum of electromagnetic radiation at a wavelength at which a first fluorochrome member of the pair is excited; however, fluorescence from the first fluorochrome that would be expected in the absence of the second fluorochrome is quenched at least in part. Unlike energy transfer pairs, however, emission at an emission wavelength of the acceptor fluorochrome is not observed. Thus, these labels comprise a pair of dyes, one of which is referred to as a "reporter," and the second of which is referred to as a "quencher." When the two dyes are held in close proximity, such as at the ends of a nucleic acid probe, the quencher moiety prevents detection of a fluorescent signal from the reporter moiety. When the two dyes are separated, however, the fluorescent signal from the reporter moiety becomes detectable. Suitable dye pairs include 6-carboxyfluorescein (FAM), tetrachloro-6-carboxyfluorescein (TET), and 2'-chloro-7'-phenyl-1,4-dichloro-6-carboxyfluorescein (VIC) as the reporter dye, and tetra-methylcarboxyrhodamine (TAMRA) 4-(4-dimethylaminophenylazo)benzoic acid ("DABCYL" or a DABCYL analog) as the quencher. Tetramethylrhodamine (TMR) or 5-carboxyrhodamine 6G (RHD) also may be combined with DABCYL.

The term "linker" as used herein refers to one or more chemical bonds or a chemical group used to link one moiety to another, serving as a divalent bridge, where it provides a group between two other chemical moieties.

The term "identifying" as used herein with respect to an amplified sample is meant that the presence or absence of a particular nucleic acid amplification product is detected. Numerous methods for detecting the results of a nucleic acid amplification method are known to those of skill in the art.

The term "real time PCR" as used herein means that a signal emitted from the PCR assay is monitored during the reaction as an indicator of amplicon production during each PCR amplification cycle (i.e., in "real time"), as opposed to conventional PCR methods, in which an assay signal is detected at the endpoint of the PCR reaction. Real time PCR is generally based on the detection and quantitation of a fluorescent reporter. The signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. For a general description of "real time PCR" see Dehée et al. J. Virol. Meth. 102:37-51 (2002); and Aldea et al. J. Clin. Microbiol. 40:1060-1062 (2002) (referring to the "LightCycler," where real-time, kinetic quantification allows measurements to be made during the log-linear phase of a PCR).

One general method for real time PCR uses fluorescent probes such as the TaqMan® probes, molecular beacons and scorpions. Real-time reverse-transcriptase (RT) PCR quantitates the initial amount of the template with more specificity, sensitivity and reproducibility, than other forms of quantitative reverse transcriptase PCR, which detect the amount of final amplified product. Real-time RT-PCR does not detect the size of the amplicon.

The TaqMan® probes (Heid et al., 1996) and molecular beacons use the fluorogenic 5' exonuclease activity of Taq polymerase to measure the amount of target sequences in cDNA samples. TaqMan® probes are oligonucleotides longer that contain a fluorescent dye usually at or near the 5' base, and a quenching moiety typically at or near the 3' base.

The quencher moiety may be a dye such as TAMRA or may be a non-fluorescent molecule such as 4-(4-dimethylaminophenylazo)benzoic acid (DABCYL). See Tyagi et al., *Nature Biotechnology* 16:49-53 (1998). When irradiated, the excited fluorescent dye transfers energy to the nearby quenching dye molecule rather than fluorescing (this is called FRET=Förster or fluorescence resonance energy transfer). Thus, the close proximity of the reporter and quencher prevents emission of any fluorescence while the probe is intact.

Multiplex TaqMan assays can be performed using multiple dyes with distinct emission wavelengths. Available dyes for this purpose are FAM, TET, and VIC, in combination with TAMRA or DABCYL and/or TMR and RHD in combination with DABCYL. Probes for detecting amplified sequence in real time may be stored frozen (−10° to −30° C.) as 100 ⊠M stocks. TaqMan MGB probes are available from Applied Biosystems (4316032). Suitable probes are shown in Table 2.

TABLE 2

Probes for detection of bcr/abl and housekeeping genes

| sequence target | Probe Name | Probe Sequence | |
|---|---|---|---|
| BCR e1a2 | BCR-P1 probe | 5'-ACACGACAACCGGGCAGTGCC-3'<br>The 5' end is labeled with FAM and the 3' end is labeled with TAMRA. | (SEQ ID NO. 8) |
| BCR b2a2/b3a2 | BCR-P2,3 probe | 5'-TGCTGTGGACAGTCTGGAGTTTCACACA-3'<br>The 5' end is labeled with FAM and the 3' end is labeled with TAMRA. | (SEQ ID NO. 9) |
| ABL | ABL-Probe: | 5-CCA GTA GCA TCT GAC TTT GAG CCT CAG GG-3'<br>The 5' end is labeled with FAM and the 3' end with TAMRA. | (SEQ ID NO. 10) |
| GAPDH | GAPDH-Probe: | 5'-CAA GCT TCC CGT TCT CAG CC-3'<br>The 5' end is labeled with FAM and the 3' end with TAMRA. | (SEQ ID NO. 11) |

TaqMan® probes are designed to anneal to an internal region of a PCR product. When the polymerase replicates a template on which a TaqMan® probe is bound, its 5' exonuclease activity cleaves the probe. This ends the activity of quencher (no FRET) and the reporter dye starts to emit fluorescence which increases in each cycle proportional to the rate of probe cleavage. Accumulation of PCR products is detected by monitoring the increase in fluorescence of the reporter dye (note that primers are not labeled). TaqMan® assay uses universal thermal cycling parameters and PCR reaction conditions. Because the cleavage occurs only if the probe hybridizes to the target, the fluorescence detected originates from specific amplification. The process of hybridization and cleavage does not interfere with the exponential accumulation of the product. One specific requirement for fluorogenic probes is that there be no G at the 5' end. A 'G' adjacent to the reporter dye quenches reporter fluorescence even after cleavage.

Products produced in a RT-PCR amplification reaction using enzyme rTth to reverse transcribe and PCR-amplify bcr/abl translocation sequences or housekeeping gene transcript sequences is described. During RT-PCR, the amplified products hybridize to probe nucleic acids, which are labeled with both a reporter dye and a quencher dye. When these two dyes are in close proximity, i.e. both are present in an intact probe oligonucleotide, the fluorescence of the reporter dye is suppressed. However, a polymerase, such as rTth, having 5'-3' nuclease activity can be provided in the RT-PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequence detection apparatus, the fluorescent signal produced by the reporter dye is detected and/or quantified. The increase in fluorescence is a direct consequence of amplification of target nucleic acids during RT-PCR.

In a preferred embodiment, real time PCR is performed using TaqMan® probes in combination with a suitable amplification/analyzer such as the ABI Prism 7900HT Sequence Detection System. The ABI PRISM® 7900HT Sequence Detection System is a high-throughput real-time PCR system that detects and quantitates nucleic acid sequences. Briefly, TaqMan™ MGB probes specific for each allele are included in the PCR assay. These probes contain a reporter dye at the 5' end and a quencher dye at the 3' end. In addition, the minor-groove binding (MGB) component at the 3' end of the probe stabilizes the specific hybridization of a TagMan™ probe to its DNA target and thus enhances the specificity of the assay. Each allele specific probe is conjugated with a different fluorescent reporter dye. During PCR, the fluorescently labeled probes bind specifically to their respective target sequences; the 5' nuclease activity of Taq polymerase cleaves the reporter dye from the probe and a fluorescent signal is generated. The increase in fluorescence signal is detected only if the target sequence is complementary to the probe and is amplified during PCR. A mismatch between probe and target greatly reduces the efficiency of probe hybridization and cleavage. The ABI Prism 7900HT Sequence detection System measures the increase in fluorescence during PCR thermal cycling, providing "real time" detection of PCR product accumulation.

Real Time detection on the ABI Prism 7900HT Sequence Detector monitors fluorescence and calculates Rn during each PCR cycle. The threshold cycle, or Ct value, is the cycle at which a statistically significant increase in ΔRn, the difference between reporter fluorescence in the sample and that in the No Template Control, is first detected.

The term "sample" as used herein refers to blood, bone marrow or other tissues in which CML or ALL or other leukemic cells with a bcr/abl translocation may reside. Generally a 1-3 mL blood sample is adequate and may be collected with heparin, EDTA, or ACD as anti-coagulant. An example of a sample suitable for the present invention is as follows: For assay, transfer 2 ml of peripheral blood drawn in EDTA or heparin anti-coagulant to 6 ml of an stabilizing agent RNA STAT-50™ LS, or TRIzol® LS (or other RNAse inhibitor), or 0.2 ml of bone marrow aspirate to 0.6 ml of stabilizing agent RNA STAT-50™ LS, or TRIzol® LS (or other RNAse inhibitor). Samples can be frozen and processed at a later time. Also included within the meaning of a "sample" is a bone marrow or other tissues in which CML or ALL cells may reside that has been processed to release or otherwise make available the nucleic acid for detection. For example, a biological sample may include a cDNA.

The term "subject" as used herein means a human or any other animal which contains a MUCOL1 gene that can be amplified using the primers and methods described herein. A subject can be a patient, which refers to a human presenting to a medical provider for diagnosis or treatment of a disease. A human includes pre and post natal forms. Particularly preferred subjects are humans being tested for the existence of a Mucolipidosis carrier state or disease state.

The term "correlating the housekeeping gene transcript signal with the amount of a leukemic cell RNA that generates the same signal" as used herein means that the PCR signal for the housekeeping gene transcript in the biological sample (i.e. patient sample) is correlated with the amount of a cell line RNA or cDNA that generates the same housekeeping gene transcript signal amplified by the same assay. This is achieved by extrapolating the housekeeping gene signal from the biological sample to a standard curve of PCR signals versus cell line RNA or cDNA obtained by amplifying using the housekeeping primers and probes of the invention. The amount of cell line RNA that has the same housekeeping gene transcript signal as in the biological sample provides a more uniform value to which bcr/abl transcript PCR signals can be compared.

A preferred cell line is one that expresses uniform high levels of the housekeeping gene. In some embodiments, the cell line would not have a bcr/abl translocation. In some embodiments, the cell line would be a leukemic cell line or lymphoma cell line. A preferred cell line is the RAJI cell line.

The term "a level of bcr/abl transcript correlating with leukemic cell number" as used herein means bcr/abl transcript detected in a patient sample using the methods of the invention as a ratio of an amount of RNA from a cell line that has a level of a housekeeping gene transcript which is the same as the level of the housekeeping gene transcript in the patient sample. The ratio may have the bcr/abl transcript value in the numerator or the denominator. An amount of RNA from a cell line that has a level of a housekeeping gene transcript which is the same as the level of the housekeeping gene transcript in the patient sample is determined by extrapolating the PCR signal for the housekeeping gene transcript in the patient sample to a standard curve of PCR signals in which the PCR housekeeping transcript signal is plotted versus the amount of cell line RNA used as template. The ratio of bcr/abl transcript to housekeeping gene transcript provides a "quantitative" value of leukemic cell load with the genetic bcr/abl translocation signature in the patient. In a preferred embodiment, the transcript may be abl or GAPDH.

Quantitative analysis of the bcr/abl major translocation is useful in monitoring residual disease and genetic recurrence after treatment. In a preferred embodiment, the same type of sample that is analyzed for a level of bcr/abl transcript correlating with leukemic cell number is used both before and after therapy.

The term "about" as used herein means in quantitative terms plus or minus 5%.

The term "substantially" as used herein means in quantitative terms 60% or more of the specified value or term.

The examples below illustrate a standard protocol for performing PCR and analyzing in real time. The TaqMan system of primer labeling is a preferred method of real time detection of PCR amplicons.

The following examples serve to illustrate the present invention. These examples are in no way intended to limit the scope of the invention.

EXAMPLES

Example 1

Detection bcr/abl Leukemic Cells in a Sample

A. Extraction of RNA

Blood or marrow is processed to extract total RNA using a commercially available RNA Extraction kit or the process described below.

1) Label one clean 15 ml sterile centrifuge tube for each blood sample, and a 1.7 ml microtube for each bone marrow sample.

2) If sample is lysed in RNA STAT-50™ LS or TRIzol® LS and shipped frozen, quickly defrost the sample by swirling in 37° C. water bath. For peripheral blood, transfer sample (8 ml) to its labeled tube using a fine bore transfer pipet.

3) For bone marrow, transfer sample (0.8 ml) to its labeled microtube using a fine bore transfer pipet.

4) If the sample is in EDTA or heparin anti-coagulant, add 2 ml of whole blood 6 ml of RNA STAT-50™ LS or TRIzol® LS; or 0.2 ml of bone marrow to 0.6 ml of RNA STAT-50™ LS or TRIzol® LS in a 1.7 ml microtube. Pipet solution up and down or vortex to homogenize the sample and leave at room temperature for 10 minutes.

5) Add 1.6 ml of chloroform to 8 ml of homogenate or 0.16 ml of chloroform to 0.8 ml of homogenate. Cap tube tightly, and shake vigorously for 15 seconds (Do not vortex). Repeat with next sample. Leave it at room temperature (15-30° C.) for 10 minutes.

6) Centrifuge 15 ml sample tubes at 3400 rpm in Eppendorf 5810R centrifuge at 4° C. for 30 minutes, or spin microtubes at 10,700 rpm in Eppendorf 541 7R centrifuge at 4° C. for 15 minutes to separate phases.

7) During centrifugation, label a new set of tubes for each sample and transfer 4 ml of isopropanol to each 15 ml tube, and 0.4 ml of isopropanol to each microtube. Change gloves.

8) Using a new fine-bore transfer pipette, transfer the aqueous phase (4 ml or 0.4 ml) to its new tube, and discard lower phase.

9) Cap tubes tightly, mix completely by inverting tubes several times, and place the samples at room temperature (20-30° C.) for 10 minutes.

10) Centrifuge samples (in 15 ml tube) at 3,400 rpm in Eppendorf 5810R centrifuge at 4° C. for 15 minutes or at 14,000 rpm in Eppendorf 5417R centrifuge at 4° C. for 10 minutes. The RNA will form a precipitate at the bottom of the tube.

11) Aspirate and discard the supernatant using a new transfer pipet, and return tube to ice.

12) Precipitate the RNA by addition of 75% cold ethanol, transferring to a new tube, centrifuging and discarding the supernatant. The pellet is then dried.

The amount of RNA is measured using a RiboGreen™ (Molecular Probes) quantification kit. This is a fluorescence based assay which can be detected using the BioLumin™ 960 instrument. The total RNA and a portion adjusted to between 10-30 ng/ul with MagNa Pure elution buffer (EB). The stock extracted total RNA is stored at −70° C. for later retesting if needed.

B. Amplification Reagents

Individual amplifications were prepared in a final volume of 50 μl, which was added to 96 well microAmp Optical reaction plates. Each amplification volume contained 5 μl of the RNA sample (generally between 10-30 ng/ul) and 45 μl of PCR master mix. PCR master mix for the various amplification assays is constituted as shown in Table 3-6. ABI 2× MMX refers to TaqMan 2× Universal Master Mix (Applied Biosystems, #4304437). All primer and probe stock concentrations were 100 μM. For best performance, the 40× enzyme mix should be added just before adding the RNA templates.

TABLE 3 bcr/abl multiplex master mix (P1, P2/P3) (Quantitative)

| Master mix component | 200 Rxn volume (20 tests) | Final concentration |
| --- | --- | --- |
| DI H2O | 3550 ul | |
| ABI 40× Enzyme Mix* | (250 ul) | 1× |
| ABI 2× MMX | 5 ml | 1× |
| 100 μM BCR-P1F (primer) | 40 ul | 400 nM |
| 100 μM BCR-P2, P3F (primer) | 40 ul | 400 nM |
| 100 μM BCR/ABL-R (primer) | 40 ul | 400 nM |
| 25 μM BCR-P1 (probe) | 40 ul | 100 nM |
| 25 μM BCR-P2, 3 (probe) | 40 ul | 100 nM |
| Total Volume | 9 ml | |

*means that component is added just before use.

TABLE 4

ABL internal control master mix (Quantitative)

| Master mix component | 200 Rxn volume (20 tests) | Final concentration |
| --- | --- | --- |
| DI H2O | 3660 ul | |
| ABI 40× Enzyme Mix* | (250 ul) | 1× |
| ABI 2× MMX | 5 ml | 1× |
| 100 μM ABL-F (primer) | 40 ul | 400 nM |
| 100 μM ABL-R (primer) | 40 ul | 400 nM |
| 100 μM ABL probe | 10 ul | 100 nM |
| Total Volume | 9 ml | |

*means that component is added just before use.

TABLE 5

BCR P1 master mix (Qualitative)

| Master mix component | 200 Rxn volume (20 tests) | Final concentration |
| --- | --- | --- |
| DI H2O | 3630 ul | |
| ABI 40× Enzyme Mix | (250 ul) | 1× |
| ABI 2× MMX | 5 ml | 1× |
| 100 μM BCR-P1F (primer) | 40 ul | 400 nM |
| 100 μM BCR/ABL-R (primer) | 40 ul | 400 nM |
| 25 μM BCR-P1 (probe) | 40 ul | 100 nM |
| Total Volume | 9 ml | |

*means that component is added just before use.

TABLE 6

BCR P2/P3 master mix (Qualitative)

| Master mix component | 200 Rxn volume (20 tests) 200 Rxn | Final concentration Final conc. |
| --- | --- | --- |
| DI H2O | 3630 ul | |
| ABI 40× Enzyme Mix | (250 ul) | 1× |
| ABI 2× MMX | 5 ml | 1× |
| 100 μM BCR-P2, P3F (primer) | 40 ul | 400 nM |
| 100 μM BCR/ABL-R (primer) | 40 ul | 400 nM |
| 25 μM BCR-P2, P3 (probe) | 40 ul | 100 nM |
| Total Volume | 9 ml | |

*means that component is added just before use.

C. Standard Curve for Quantification

A six-point 10 fold serial dilution standard curve is used for quantification. A six-point standards by making 10 fold serial dilutions of RAJI RNA stock (Burkitt lymphoma) (1 mg/ml) in pH 7.0 TE buffer. The standard curve range includes the following amounts: 5 ug, 500 ng, 50 ng, 5 ng, 500 pg, and 50 pg. The standards are used as template with the ABL primer set and ABL probe. One standard curve is used to quantify both ABL and bcr/abl of controls and patient samples. The R-squared value for the standard curve should be ≧0.95. Up to one full standard or 2 singlicate may be deleted. The RT-PCR may need to be repeated if R-squared value is less than 0.95.

D. Controls

Controls for each bcr/abl multiplex RT-PCR assay may include K562 for P2P3 transcript (high positive and low positive), Sup-B15 for P1 transcript, a negative (normal; e.g. RAJI) and a no template multiplex master mix control. An ABL internal control well (ABL or GAPDH) also is included. Positive amplification for all internal control wells should be obtained except for the no template control. If the internal control fails to amplify, the test should be repeated and, there may be a need to investigate the quality or quantity of the RNA template used.

bcr/abl transcript typing is preformed on a qualitative basis using the RT-PCR assay with two single primer pair master mixes instead of one multiplex with two sets of primer pairs. Each master mix to transcript typing amplifies p1 or the p2p3. The transcript typing qualitative assays should include positive controls (k562 for p2p3 and Sup-B15 for p1), negative control and no template control.

TABLE 7

Amplification controls

| Control | Preparation |
| --- | --- |
| Negative (Normal) | 10 ug/ml Raji total RNA. |
| K562 high control (b2a2/b3a2) | 1:10 dilution of K562 RNA (approx. 15 ug/ml) with 10 ug/ml Raji RNA. Expected ratio: 2.0-5.0 |
| K562 low control (approx. 0.01% of K562) sensitivity control | 1:100 dilution of High Pos Control with 10 ug/ml Raji RNA. Expected ratio: 0.01-0.1 |
| Sup-B15 (e1a2) | 1:50 dilution of Sup-B15 total RNA. (approx. 13 ug/ml) Expected ratio: 0.4-2.0 |

TABLE 8

Multiplex RT-: PCR (quantitative Assay) control results

| Control | Expected Result |
|---|---|
| Master Mix Control (NTC) | No amplification in both bcr/abl and ABL reactions. |
| Negative (Normal) | No amplification in bcr/abl reaction and positive amplification in ABL reaction. |
| High (K562) (b2a2/b3a2) | Positive amplification seen in both ABL and bcr/abl reactions. BCR/ABL ratio has to be within established range. |
| Low(K562) (b2a2/b3a2) | Positive amplification seen in both ABL and bcr/abl reactions. BCR/ABL ratio has to be within established range. |
| Sup-B15 (e1a2) | Positive amplification seen in both ABL and bcr/abl reactions. BCR/ABL ratio has to be within established range. |

TABLE 9

RT-: PCR (qualitative) transcript typing control results

| Control | Expected Result |
|---|---|
| Master Mix Control (NTC) | No amplification in both bcr/abl and ABL reactions. |
| Negative (Normal) | No amplification in bcr/abl reaction and positive amplification in ABL reaction. |
| High (K562) (b2a2/b3a2) | Positive amplification seen in both ABL and BCR p2p3 reaction. No amplification in BCR p1 reaction. |
| Sup-B15 (e1a2) | Positive amplification seen in both ABL and BCR p1 reaction. No amplification in BCR p2p3 reaction. |

E. Amplification Procedure and Analysis

Following addition of RNA and PCR master mix, wells were tightly sealed with an optically transparent adhesive cover. The plate was centrifuged at ~1600 rpm for 15 seconds to ensure that the added volumes were combined.

The plate was subject to PCR with real time analysis using an ABI 7900 HT instrument according to the manufacturing instructions. PCR was conducted using the following temperature profile: For cDNA, the profile is step 1: 95° C. for 10 minutes; step 2: 95° C. for 15 seconds; step 3: decrease to 60° C. for one minute; step 4: repeat step 2 and 3 for 40-44 times. For RNA, step 1: 50° C. for 30 minutes; step 2: 95° C. for 10 seconds; step 3: 95° C. for 15 seconds; step 4: decrease to 60° C. for one minute; step 5: repeat step 3 and 4 for 40-44 times.

Real time detection on the ABI PRISM 7900HT sequence detector monitors fluorescence during amplification and calculates Rn during each cycle. Rn is the difference between reporter fluorescence in the sample and that in a no template control. The threshold cycle or Ct value is the cycle at which a statistically significant increase in Rn if first detected.

The results were analyzed using software available with the ABI PRISM 7900HT Sequence Detection System, using version 2.1 software. Data are collected are then analyzed automatically using the software. The processed genotype results are downloaded into a laboratory information management system with the following output.

The quantity of ABL and bcr/abl transcripts from the multiplex quantitative assay are calculated by ABI PRISM 7900HT software based on the standard curve (Ct value vs. starting quantity). A results table is exported to EXCEL. A normalized target value (BCR/ABL ratio) is then calculated by dividing the quantity of bcr/abl transcripts by the quantity of ABL $$BCR/ABL \text{ Ratio} = \frac{bcr/abl \text{ Quantity}}{ABL \text{ Quantity}}$$

The ratio may use GAPDH in the denominator in place of ABL. All control and patient RNA samples should have a positive ABL amplification. If there is no bcr/abl amplification, the ratio should be zero, the results should be reported as "Negative". Amplification plot and multicomponent plot should be reviewed on all reaction wells with a CT values less than 45 to ensure that the crossing point is not caused by the background fluorescence.

If the samples with bcr/abl or ABL quantity are off curve high, and one cannot extrapolate to have an accurate value, then the patient RNA should be repeated using further dilution (1:10, 1:100 or 1:1000). If the standard curve $R^2$ value (Fit R)<0.95, then one should delete up to 1 full standard or 2 singlicate standards, or repeat the assay.

The qualitative assay evaluating the presence of the particular bcr/abl transcript may use gel electrophoresis to evaluate RNA transcript size from the PCR product. The e1a2 (P1) transcript is about 219 bp, the b2a2 (P2) transcript is about 124 bp and the b3a2 (P3) transcript is about 199 bp. The internal control can be run on gel to assess the quality and quantity of the RNA. The PCR product of GAPDH run on NuSieve 3:1 agarose gel is 226 bp. FIG. 3 of U.S. Ser. No. 09/747,165 illustrates an agarose gel in which the top lane M are size markers, the lane below it SUPB15 illustrates the band position of the e1a2 PCR product K562 illustrates the band position of b3a2 and BC9-515 illustrates the band position of b2a2. The remaining lanes with BC9-516, 519, 518, 517, 274, 273 and 272 are samples which had unknown PCR bcr/abl gene translocation products.

The output from the RT-PCR assay can the conversion of the bcr/abl detected signal transcript into a leukemic cell number. This can be done using a standard curve using a bcr/abl translocation positive leukemic cell line (e.g. K562). The standard curve is a plot of leukemic cell line cell number versus bcr/abl transcript signal obtained using RNA (or cDNA) for each quantity of leukemic cell line cells used. For example, FIG. 1 of U.S. Ser. No. 09/747,165 shows a standard curve created using six duplicates FAMA1-A2, etc. of standard dilutions of leukemia cells resulting in six curves. The point where each curve crosses the threshold line (see arrow) indicates the Cycle threshold or CsubT for each sample. Theory predicts that the difference between each serial dilution curve should be 3.5. Comparison of FAM A1/A2 with FAMA3/A4 shows this result to fairly good accuracy (21.150-17.828=3.32). Also, the reproducibility between samples A1 (17.828) and A2 (17.615; A3 and A4 etc. is shown. FIG. 2 of U.S. Ser. No. 09/747,165 shows a standard curve created from the curve in FIG. 1 which allows for interpretation of the quantity of leukemic cells in an unknown sample. The assay can reliably detect one K562 cell in ten milliliters of whole blood. Normally, there is 5-7×10$^6$ leukocytes in one milliliter of human whole blood.

However, any units and any physical characteristics which allow for the medically or biochemically relevant comparison of different samples with respect to bcr/abl translocations and diagnosis of leukemia, in particular, CML and/or ALL are within the scope of the present invention. For example, the ratio of bcr/abl signals in, for example, fluorescence units such as threshold cycle or CsubT units to CsubT units of an internal signal from a universally expressed gene.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. The term "consisting essentially of" when used in connection with nucleotide sequence shall mean the specified sequence and other sequences which have relatively minor difference that do not effect the function of the sequence for its intended purpose. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for detecting the presence of a major breakpoint and/or minor breakpoint bcr/abl translocation in a biological sample, comprising:
   (a) preparing a nucleic acid mixture comprising
      (i) RNA or cDNA from the biological sample;
      (ii) three or more oligonucleotide primers together capable of amplifying at least one major breakpoint bcr/abl translocation transcript and at least one minor breakpoint bcr/abl translocation transcript;
      (iii) a first oligonucleotide probe specific for the bcr region of the minor bcr/abl translocation transcript amplified by said primers; and,
      (iv) a second oligonucleotide probe specific for the bcr region of the major bcr/abl translocation transcript amplified by said primers,
   wherein the first and second probes are each labeled with a different detectable label;
   (b) conducting a multiplex amplification reaction with a DNA polymerase using the mixture; and
   (c) detecting hybridization of the first probe or the second probe to the amplification product of step (b), wherein hybridization of the first probe indicates the presence of a minor breakpoint bcr/abl translocation, and hybridization of the second probe indicates the presence of a major breakpoint bcr/abl translocation.

2. The method of claim 1, wherein said detecting is performed in real time.

3. The method of claim 1, wherein said primers comprise the sequences of SEQ ID NOs: 1-3.

4. The method of claim 1, wherein said first probe comprises the sequence of SEQ ID NO: 8.

5. The method of claim 1, wherein said second probe comprises the sequence of SEQ ID NO: 9.

6. The method of claim 1, wherein said primers comprise the sequences of SEQ ID NOs: 1-3, said first probe comprises the sequence of SEQ ID NO: 8, and said second probe comprises the sequence of SEQ ID NO: 9.

7. The method of claim 1, wherein at least one of said detectable labels is a molecular beacon pair.

8. The method of claim 1, wherein said molecular beacon pair comprises 2'-chloro-7'-phenyl-1,4-dichloro-6-carboxyfluorescein (VIC), 6-carboxyfluorescein (FAM) or tetrachloro-6-carboxyfluorescein (TET), in combination with a quencher moiety.

9. The method of claim 8, wherein said DNA polymerase further comprises a 5' exonuclease activity.

10. The method of claim 1 further comprising determining a level of a housekeeping gene transcript present in the biological sample, comprising:
    (d) contacting the RNA or cDNA with a primer pair for amplifying a housekeeping gene transcript and detectably-labeled probe for the amplified housekeeping gene transcript;
    (e) conducting an amplification reaction to amplify the housekeeping gene transcript; and
    (f) monitoring the accumulation of amplified housekeeping gene transcript by detecting the probe, wherein an increase in housekeeping gene transcript indicates the presence of the housekeeping gene transcript in the biological sample.

11. The method of claim 10 further comprising the step of correlating the amount of amplified housekeeping gene transcript with the amount of a cell line RNA or cDNA that generates the same housekeeping gene signal, said correlating a result of extrapolating the housekeeping gene signal from the biological sample to a standard curve of PCR signals versus cell line RNA or cDNA.

12. The method of claim 11 wherein the cell line RNA is from a leukemic cell line.

13. The method of claim 10 wherein said housekeeping gene transcript is an abl or a GAPDH transcript.

14. The method of claim 10 wherein said housekeeping gene transcript is amplified in the same amplification reaction as the bcr/abl translocation transcripts.

15. The method of claim 3, wherein if the presence of a major breakpoint bcr/abl translocation is detected by hybridization of the second probe to the amplification product of step (b), the amplified product is evaluated by gel electrophoresis to distinguish the size of the amplified product, wherein a size of about 124 bp indicates the b2a2 translocation and a size of about 199 bp indicates the b3a2 translocation.

16. A method for determining the presence or absence of CML or AML cells in a biological sample, comprising:
    (a) preparing a nucleic acid mixture comprising
        (i) RNA or cDNA from the biological sample;
        (ii) three or more oligonucleotide primers together capable of amplifying at least one major breakpoint bcr/abl translocation transcript and at least one minor breakpoint bcr/abl translocation transcript;
        (iii) a first oligonucleotide probe specific for the bcr region of the minor bcr/abl translocation transcript amplified by said primers; and,
        (iv) a second oligonucleotide probe specific for the bcr region of the major bcr/abl translocation transcript amplified by said primers,
    wherein the first and second probes are each labeled with a different detectable label;
    (b) conducting a multiplex amplification reaction with a DNA polymerase using the mixture; and
    (c) detecting hybridization of the first probe or the second probe to the amplification product of step (b), wherein hybridization indicates the presence of CML or AML cells in the biological sample.

17. The method of claim 16, wherein said detecting is done is real time.

18. The method of claim 16, wherein said biological sample comprises blood or bone marrow.

19. The method of claim 16, wherein said primers comprise the sequences of SEQ ID NOs: 1-3.

20. The method of claim 16, wherein said first probe comprises the sequence of SEQ ID NO: 8.

21. The method of claim 16, wherein said second probe comprises the sequence of SEQ ID NO: 9.

22. The method of claim 16, wherein said primers comprise the sequences of SEQ ID NOs: 1-3, said first probe comprises the sequence of SEQ ID NO: 8, and said second probe comprises the sequence of SEQ ID NO: 9.

23. The method of claim 16, wherein said detectable label is a molecular beacon pair.

24. The method of claim 16, wherein said molecular beacon pair comprises 2'-chloro-7'-phenyl-1,4-dichloro-6-carboxyfluorescein (VIC), 6-carboxyfluorescein (FAM) or tetrachloro-6-carboxyfluorescein (TET), in combination with a quencher moiety.

25. The method of claim 23, wherein said DNA polymerase further comprises a 5' exonuclease activity.

26. A method for detecting the presence of a major breakpoint and/or minor breakpoint bcr/abl translocation in a biological sample, comprising:
    (a) preparing a nucleic acid mixture comprising
        (i) RNA or cDNA from the biological sample;
        (ii) oligonucleotide primers of SEQ ID NOs: 1-3;
        (iii) a first oligonucleotide probe of SEQ ID NO: 8; and,
        (iv) a second oligonucleotide probe of SEQ ID NO: 9,
    wherein said first and second probes are each labeled with a different detectable label;
    (b) conducting a multiplex amplification reaction with a DNA polymerase using the mixture; and
    (c) detecting hybridization of the first probe or the second probe to the amplification product of step (b) in real time, wherein hybridization of the first probe indicates the presence of a major breakpoint bcr/abl translocation, and hybridization of the second probe indicates the presence of a minor breakpoint bcr/abl translocation.

27. The method of claim 26, wherein said DNA polymerase further comprises a 5' exonuclease activity capable of degrading the first probe and/or the second probe when hybridized to an amplified nucleic acid, during the amplification reaction.

28. The method of claim 26, wherein said molecular beacon pair comprises 2'-chloro-7'-phenyl-1,4-dichloro-6-carboxyfluorescein (VIC), 6-carboxyfluorescein (FAM) or tetrachloro-6-carboxyfluorescein (TET), in combination with a quencher moiety.

* * * * *

SEQUENCE LISTING

<160> NUMBER OF SEQ ID NOS: 14

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcgcagaac tcgcaaca                                                   18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gagctgcaga tgctgaccaa                                                 20

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcagaccctg aggctcaaag tc                                              22

<210> SEQ ID NO 4
<211> LENGTH: 23
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 4
tcctccagct gttatctgga aga                                              23

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgggtccagc gagaaggtt                                                   19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaggtgaag gtcggagtc                                                   19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaagatggtg atgggatttc                                                  20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
acacgacaac cgggcagtgc c                                                21

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tgctgtggac agtctggagt ttcacaca                                         28

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
```

```
                                -continued
         probe

<400> SEQUENCE: 10
ccagtagcat ctgactttga gcctcaggg                                     29

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
         probe

<400> SEQUENCE: 11
caagcttccc gttctcagcc                                               20

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
         oligonucleotide

<400> SEQUENCE: 12
ctgcccacag tacc                                                     14

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence: Synthetic
         oligonucleotide

<400> SEQUENCE: 13
tgcccacggt acc                                                      13

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
         oligonucleotide

<400> SEQUENCE: 14
acccaggccc acat                                                     14
```